United States Patent [19]

Baker et al.

[11] Patent Number: 4,891,847
[45] Date of Patent: Jan. 9, 1990

[54] METHOD AND APPARATUS FOR REDUCING INCONTINENCE OR PAIN

[76] Inventors: Glenn R. Baker; Janet B. G. French, both of 70 Glen Dr., Worthington, Ohio 43085

[21] Appl. No.: 106,895

[22] Filed: Oct. 9, 1987

Related U.S. Application Data

[63] Continuation of Ser. No. 858,818, May 2, 1986, abandoned.

[51] Int. Cl.⁴ .......................... A61F 5/34; A61F 13/00; A61G 9/00
[52] U.S. Cl. ........................................... 4/239; 4/244; 4/456; 4/661; 5/431; 5/436; 28/118.1; 28/120.1; 28/847
[58] Field of Search ................ 5/441, 448, 434, 432, 5/436, 463, 466; 16/124; 4/244, 456, 450, 452, 661; 128/117, 118, 845, 847; 297/455; 441/131, 130

[56] References Cited

U.S. PATENT DOCUMENTS

| | | |
|---|---|---|
| D. 160,033 | 9/1950 | Thomas . |
| D. 212,327 | 10/1968 | Brewer . |
| 458,775 | 12/1836 | Rock .................................. 128/283 |
| 467,923 | 2/1882 | Crandall ................................. 4/356 |
| 797,707 | 8/1905 | Pearson .................................. 4/356 |
| 1,468,072 | 9/1923 | Ogle .................................. 128/132 R |
| 1,503,425 | 6/1923 | Martin ................................... 4/234 |
| 1,886,637 | 11/1932 | Buckley ............................. 5/441 X |
| 2,405,484 | 8/1946 | Bailhe ................................... 5/448 |
| 2,663,020 | 12/1953 | Cushman ........................ 128/132 R |
| 2,671,226 | 3/1954 | Lychenheim .......................... 4/239 |
| 2,785,419 | 3/1957 | Walker .................................. 5/448 |
| 3,050,748 | 8/1962 | Deutinger ......................... 5/436 X |
| 3,848,281 | 11/1974 | Mathews ............................... 5/436 |
| 4,080,968 | 3/1978 | Neilson ............................... 128/292 |
| 4,133,061 | 1/1979 | Hurd .................................... 16/124 |
| 4,161,794 | 7/1979 | Darnfors .............................. 5/441 |
| 4,190,918 | 3/1980 | Harvell ............................. 5/466 X |
| 4,468,824 | 9/1984 | O'Hanlan .......................... 5/441 X |
| 4,567,887 | 2/1986 | Couch, Jr. ....................... 128/118.1 |

OTHER PUBLICATIONS

Photograph of "Donut", inflatable cushion commercially available.

*Primary Examiner*—Henry K. Artis
*Attorney, Agent, or Firm*—Ronald P. Kananen

[57] ABSTRACT

A device for reducing the risk of human incontininence while moving between a first standing position and a second seated position having an annular cushion structurally adapted for the posterior portion of a human while either in the first standing position or the second seated position. The device includes a ring-like member defining an opening therein to accommodate the seat of a commode and has straps for securing the cushion to the posterior of a human during movement between the second and first positions. A method of using the device is also disclosed which utilizes wrapping straps around the annular cushion and holding the cusion in firm contact with the posterior of the person by holding together opposite ends of each strap while in the first position and maintaining the firm contact when the person moves to the second position.

12 Claims, 2 Drawing Sheets

METHOD AND APPARATUS FOR REDUCING INCONTINENCE OR PAIN

This application is a continuation, of application Ser. No. 858,818, filed May 2, 1986 now abandoned.

BACKGROUND OF THE INVENTION

This invention relates to a method and apparatus for reducing a risk of human incontinence while moving between a standing position and a seated position, especially following childbirth or an operative procedure. More particularly, this invention relates to a method of using a generally annular cushion, referred to in the art as a "donut," for reducing incontinence or pain while moving as described above, wherein the cushion is structurally adapted to be accommodated to and held against the posterior portion of the human anatomy. Still more particularly, this invention relates to an annular cushion which is structurally adapted for comfortably contacting the posterior portion of a human by use of fixed or separable handles to permit its use to aid in controlling bladder and bowel functioning while moving between a standing position and a seated position.

A number of situations occur which affect an ability of a human to control incontinence or elimination for various reasons. The elimination of fluid wastes involves the passage of urine from the kidneys through ureters for discharge through the urethra by controlling bladder function so that initiation of urination is voluntary. Similarly, the voluntary control of the excretory function to control defecation and the excretion of fecal matter by controlling anal sphincters is highly desirable to avoid incontinence and subsequent soiling of clothing, social offense, and embarassment. A number of situations occur in which voluntary control of these bodily functions is inhibited. For example, following childbirth, or a hemorrhoid operation, or other lower abdominal treatment or surgery, a post-operative patient may experience difficulty in controlling those functions resulting in incontinence. For this purpose, a number of approaches have been developed in the art, such as adult diapers, and other physical devices which are intended to contain the bodily wastes.

An annularly-shaped device, referred to as a donut, is available in the art and is prescribed for assisting a patient following a hemorrhoid operation. The donut includes a plastic circular or a circularly-shaped device, shaped like an inner tube and having a generally circular cross-section. Such a device may be inflatable. Such a device is intended to be placed upon a seat, or on the seat of a toilet to provide comfort to the patient while eliminating bodily wastes during the period of post-operative recovery from hemorrhoid surgery. Such air cushions are flexible, substantially tubular, and contoured in shape to conform to the toilet seat or commode seat opening. Often, such devices are made of a sheet plastic, suitable for cleaning by laving with an alcohol solution.

The use of such a device normally involves placing the cushion on the seat wherein the post-operative patient moves carefully from a standing position to a seated position. In many instances, such movement is risky in that the exertion of muscle control in such movement may cause an inadvertent relaxation of the muscles controlling either elimination function resulting in "accidents" during such movement. It is a primary objective of this invention, therefore, t provide an improvement on the donut known to the art to assist in avoiding such inadvertent loss of muscular control while moving from the standing to the seated position.

It is an additional object of this invention to provide a method of using a generally annular cushion in a way which reduces incontinence or pain while moving from a first standing position to a second seated position.

It is an additional object of this invention to provide a method of using a generally annular cushion which has been structurally adapted to be accommodated by handles to the posterior portion of a human, thus to permit exertion for movement while exercising muscular control of the waste elimination functions during such movement.

It is an additional object of this invention to provide such a method which involves the steps of grasping the handle, whether fixed or attached to an annular cushion, to secure the cushion to the buttocks of the patient in a secure manner during movement from the standing to the seated position.

It is an additional object of this invention to provide an improved cushion of the type described for reducing the risk of human incontinence by providing an annular cushion structurally adapted for securely contacting a posterior of a human with means for securing the cushion to the human during such movement.

These and other objects of the invention will become apparent from the detailed description of the invention which follows.

BRIEF SUMMARY OF THE INVENTION

Directed to achieving the foregoing objects of the invention and overcoming the problems of incontinence for post-operative patients as described above, in one aspect, the invention relates to a method of using a generally annular cushion for reducing incontinence or pain while moving from a first standing position to a second seated position. The cushion is structurally adapted to be accommodated to the posterior portion, or buttocks, of a human. The cushion defines an opening therein and further includes means for removably securing the cushion to the posterior of the human during movement between the first standing position and the second seated position. The method comprises the steps of grasping the securing means on the cushion by at least a hand of the human; moving the cushion into firm contact with the posterior of the human while continuing to grasp the securing means; and moving between the first position and the second position while continuing to grasp the securing means and maintain the cushion in contact with the posterior of the human; thus reducing the risk of incontinence or pain. In one embodiment, the securing means are an integral part of the cushion. In another embodiment, the securing means comprise handles removably secured about the circumference of spaced, opposed portions of the annular cushion and have hand grips for receiving the hands of the user to secure the cushion against the posterior portion as described.

In another aspect, the invention relates to a device, similar to the donut known to the art, for reducing the risk of human incontinence while moving between a first standing position and a second seated position. The device comprises an annular cushion structurally adapted for comfortably contacting a posterior portion of a human while in either the first standing position or in the second seated position. The annular cushion comprises a ring-like member defining an opening therein to be accommodated on the seat of a commode. According to the invention, means are provided for securing the cushion to the posterior of a human during movement between the first position and the second position. In a first embodiment, the securing means includes a handle member fixed to the cushion and securely adapted to be gripped by the hand of a human. Preferably, the handle with its gripping portion for accommodating the hand of the user is integrally formed as a part of the cushion and is directed generally axially parallel to the axis of the annular cushion. In an alternative embodiment, removable straps having a length sufficient to envelop a substantial portion of the periphery or circumference of the annular cushion are provided. The straps include grips at the opposed ends thereof so that when the strap envelops the cushion, the grips may be together secured by the hand of the user at spaced opposed sides of the annular cushion whereupon the cushion may be drawn against the posterior or buttocks of the human.

In use, such a device is positioned against the posterior or buttocks of the human while in the standing position and firmly retained in that location while moving from a standing to a seated position. The use of the device according to the invention in such a manner substantially reduces a risk of incontinence or pain during such movement, particularly for post-operative patients, such as following childbirth or hemorrhoid surgery.

These and other aspects of the invention will become apparent from the written description of the preferred embodiments of the invention which follows.

BRIEF SUMMARY OF THE DRAWINGS

In the drawings:

FIG. 7 illustrates that the device continues to be secured to the posterior while moving from the standing to the seated position; and FIG. 8 shows the positioning of the device while a person is in the seated position.

DETAILED DESCRIPTION OF THE PREFERRED EMBODIMENT

Figure 1:
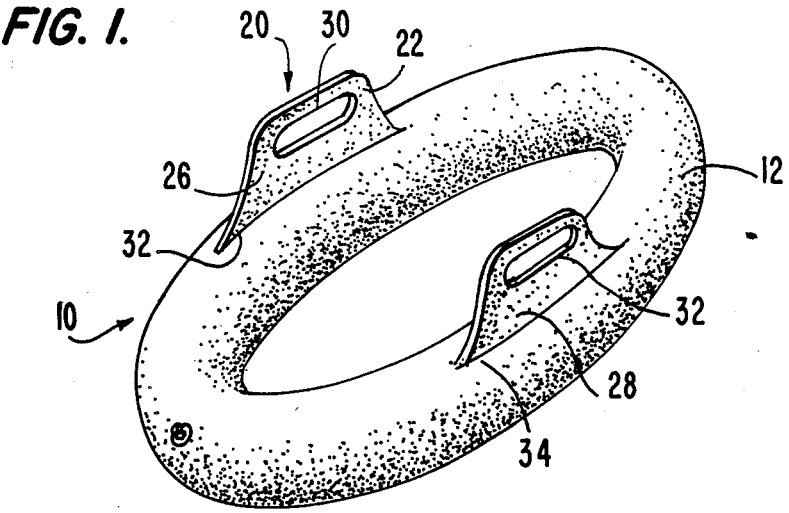
FIG. 1 is a perspective view of an annular cushion structurally adapted with fixably secured handles according to the invention.
Figure 2:
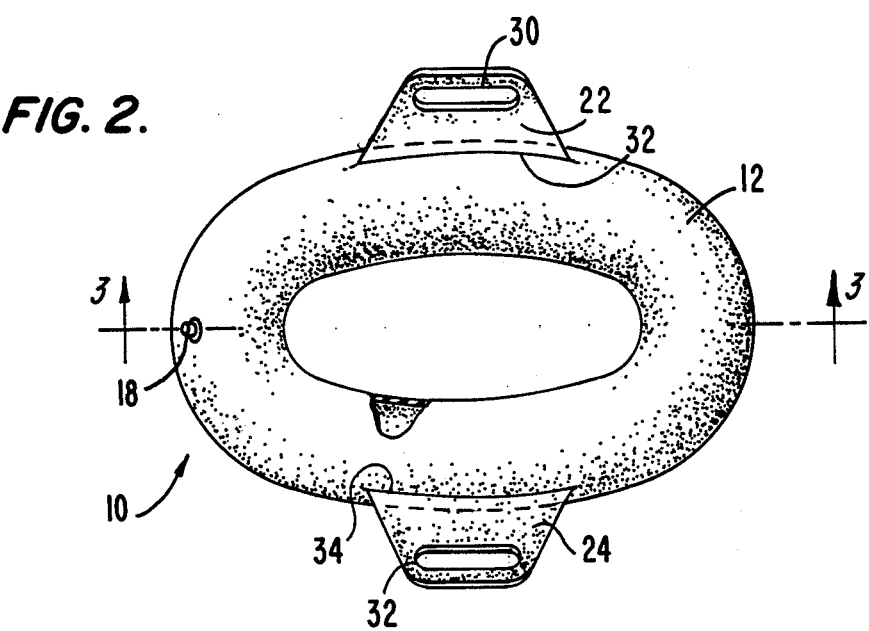
FIG. 2 is a top plan view of the device of FIG. 1.
Figure 3:
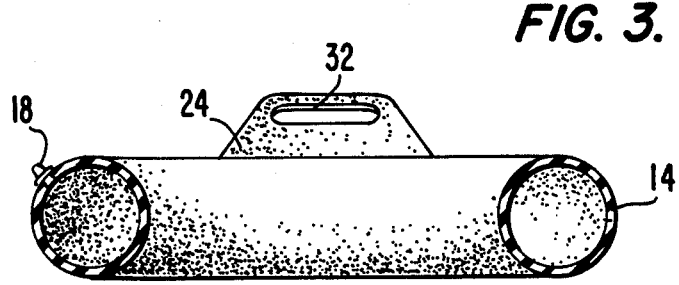
FIG. 3 is a side cross-sectional view taken along line 3—3 of FIG. 2.

As seen in FIGS. 1–3, a first embodiment of the device according to the invention is designated generally by the reference 10. The device 10 includes an annular cushion 12 made from a plastic material such as a suitable plastic or vinyl, to facilitate its cleaning by the use of alcohol or other cleaning agent. The device 10 is generally annularly-shaped, having a circular cross-section 14, as shown in FIG. 3. The cushion 10 is generally circular or slightly acircular, thus defining an opening 16 therein for use in cooperation with a toilet seat. As is known in the art, such a device may be collapsible and inflated through a valve 18 and in the foregoing respects is substantially identical to the well-known "donut" especially prescribed for use by patients recovering from hemorrhoid surgery. Such a device is usually hollow, as shown in FIG. 3, but may be made in a permanent configuration wherein the interior is filled with a foamed plastic, or the cross-section is solid, such as when made from a polyethylene or polyurethane foam material.

Figure 6:
FIGS. 6–8 illustrate the steps for the use of the devices of FIGS. 1–5 wherein the improved cushion is secured to the posterior of a patient while in a standing or semi-standing position, as shown in FIG. 6.
Figure 7:
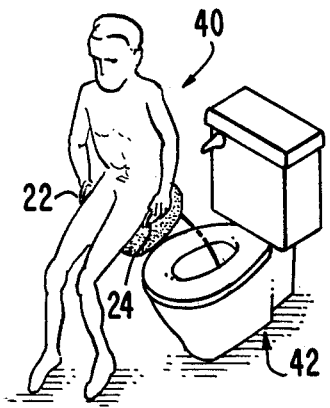
Figure 8:
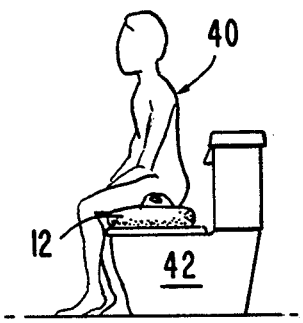

The improvement according to the invention includes means, designated generally by the reference numeral 20, for securing the cushion 10 to the posterior of the human while moving between a first standing and a second seated position as shown in FIGS. 6–8. In the first embodiment of FIG. 1, the securing means 20 includes a pair of spaced opposed handles 22, 24, each respectively having a body portion 26, 28 defining a gripping portion 30, 32 therein. The gripping portions are elongated and define an opening suitable for receiving the respectively opposed hands of the user simultaneously. Preferably, the handles 22 and 24 are secured fixedly in a conventional manner at the surfaces 32 and 34 of the cushion 12. The handles 22 and 24 are preferably generally narrower in width and somewhat elongated so that the handles 22 and 24 have a plane directed generally in parallel or slightly obliquely to the axis of the annular cushion 12. Orientation of the handles 22, 24 on the complementary surfaces of the cushion 12 in a spaced opposed manner facilitates grasping of the handles by the user to secure the cushion 12 firmly against a posterior portion of the anatomy.

As shown in FIG. 2, the planes on the handles 22, 24 may also lie slightly obliquely to the axis 36 of the annular cushion 12. With the oblique orientation shown in plan view in FIG. 2, the cushion, in use, will slightly envelop the posterior or buttocks of the user to maximize comfort.

The use of such a device is described in FIGS. 6–8. As shown in FIG. 6, a representative human patient 40 has grasped the handles 22, 24 secured to the cushion 12 while in a standing or semi-standing position prior to the use of a toilet 42. The cushion 12 is drawn firmly and securely against the posterior or buttocks of the user 40 and maintained in such a position, as shown in FIG. 7, while moving from the standing to the seated position. As a result of being so secured, the human 40 is able to exert control over the urinary and defecatory functions and control elimination of urine or defecatory matter to avoid an incident of soiling or embarassment. FIG. 8 shows the use of the device 10 during the controlled waste elimination function.

Figure 4:
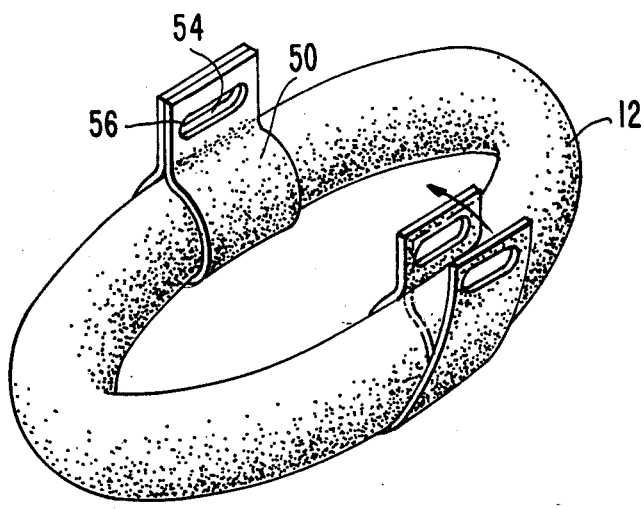
FIG. 4 is view of an alternative embodiment involving straps for enveloping spaced, opposed portions of the annular cushion.
Figure 5:
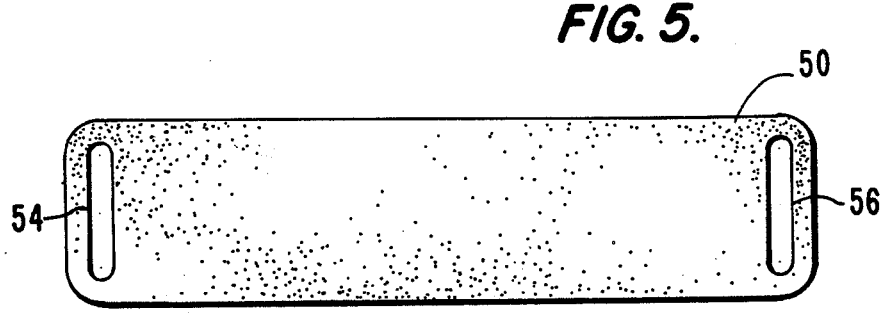
FIG. 5 is a top plan view of one of such straps for use as described in connection with FIG. 4.

FIGS. 4 and 5 illustrate an alternative embodiment. As there shown, a pair of straps are shown, each having a body 52 defining a length and a narrower width which defines openings 54 and 56 at the opposed spaced portions thereof. The strap 50 has a length sufficient to envelop the entire periphery of the annular cushion 12 so that the openings 54 and 56 may be brought into register for simultaneously receiving a hand of the user. A pair of such straps 50 are used, as shown in FIG. 4, and are preferably spaced on opposed portions of the annular cushion so that the long axes of registered openings 54 and 56 may be directed generally perpendicular to the axis of the annular cushion. The straps 50 may be made of any suitable material having a strength sufficient to draw the annular cushion 12 against the patient as described and securely retain the annular cushion 12 in that position.

When the straps 50 are positioned as shown in FIG. 4, the device is used as described in FIGS. 6-8, similar to the manner in which the device of FIGS. 1-3 having fixed handles is used.

The method and apparatus according to the invention provide significant advantages for reducing incontinence or pain for a person moving from a standing position to a seated position during a period of post-operative or post-childbirth recovery when the muscle control function is potentially inhibited. The use of such device as described in the manner described substantially assists in the patient retaining voluntary control of the bodily waste elimination function during such movement.

Having thus described the present invention in terms of particular embodiments, it will be readily apparent to those having ordinary skill in the art that numerous modifications can be made to these embodiments without deviating from the spirit and intended scope of the invention.

What is claimed is:

1. A method of using a generally annular cushion for reducing incontinence or pain while moving from a first standing position to a second seated position, said cushion being structurally adapted to be accommodated to the posterior portion of a human, defining an opening therein, and having handles positioned on opposite sides of the opening for removably securing said cushion to the posterior of said human during movement between said first position and said second position, comprising the steps of:

grasping said handles on said cushion by the hands of the human;

moving said cushion into contact with the posterior of said human while continuing to grasp said handles; and moving between said first position and said second position while continuing to grasp said handles and maintain said cushion in contact with the posterior of said human;

thereby reducing a risk of incontinence and pain during such movement.

2. The method as set forth in claim 1 further including the step of releasing the grasp of said handles upon reaching said second seated position.

3. The method as set forth in claim 1 wherein said handles are removably secured to said cushion, and the method further includes the steps of securing said handles to said cushion.

4. The method of claim 1, wherein the cushion has annular shape.

5. The method as set forth in claim 1, wherein said annular cushion defines a central axis, and said handles are fixed to said annular cushion, said handles extending from said annular cushion in a direction generally parallel to said axis.

6. The method as set forth in claim 1, wherein said annular cushion defines a central axis, and said handles are fixed to said annular cushion, said handles extending from said annular cushion in a direction oblique to said axis.

7. A device for reducing a risk of human incontinence while moving between a first standing position and a second seated position, comprising:

an annular cushion structurally adapted for comfortably contacting a posterior portion of a human while in either said first position or said second position, said annular cushion comprising a ring-like member defining an opening therein; and a pair of elongated straps defining gripping portions at the opposed end thereof, said straps being separate from said annular cushion and wrapped around said annular cushion at opposed, spaced portions thereof so that the gripping portions of each of said straps respectively are positioned in register for receiving a hand of the user.

8. The device as set forth in claim 7 wherein said cushion is inflatable.

9. The device as set forth in claim 7 wherein said cushion is solid.

10. The device as set forth in claim 7 wherein said cushion is a donut.

11. A method of reducing incontinence or pain in a person while the person moves between a first position and a second position, comprising:

wrapping straps around an annular cushion defining an opening so that an end of each strip extends through the opening in the cushion;

holding the cushion in firm contact with the posterior of the person by holding together opposite ends of each strap and drawing the cushion against the posterior while the person is in the first position; and maintaining the firm contact while the person moves from the first position to the second position.

12. The method of claim 11, wherein the opposite ends of each strap are held together by positioning an opening in one end of each strap in registration with an opening in an opposite end of the strap and extending a portion of a hand through each registered pair of openings.

* * * * *